United States Patent [19]

Renth et al.

[11] 3,941,789

[45] Mar. 2, 1976

[54] N-ARYL-N'-(PHENYL-OR PHENOXY-ALKYL)-PIPERAZINES AND SALTS THEREOF

[75] Inventors: Ernst-Otto Renth; Anton Mentrup; Kurt Schromm, all of Ingelheim am Rhein; Peter Danneberg, Ockenheim, all of Germany

[73] Assignee: Boehringer Ingelheim GmbH, Ingelheim am Rhein, Germany

[22] Filed: Dec. 21, 1973

[21] Appl. No.: 427,367

[30] Foreign Application Priority Data
Dec. 23, 1972 Germany............................ 2263211

[52] U.S. Cl. 260/268 BC; 260/243 R; 260/256.4 C; 260/256.4 N; 260/256.4 R; 260/260; 260/268 BQ; 260/268 H; 260/268 PH; 424/250
[51] Int. Cl.² ................................. C07D 241/02
[58] Field of Search... 260/268 BC, 268 BQ, 268 H, 260/268 PH

[56] References Cited
UNITED STATES PATENTS

| | | | |
|---|---|---|---|
| 3,530,131 | 9/1970 | de Stevens................... | 260/268 H |
| 3,562,277 | 2/1971 | Hansen et al.................. | 260/268 BC |

*Primary Examiner*—Richard J. Gallagher
*Assistant Examiner*—James H. Turnipreed
*Attorney, Agent, or Firm*—Hammond & Littell

[57] ABSTRACT
Compounds of the formula

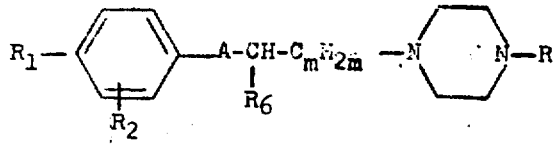

wherein
R is phenyl; phenyl having one or more substituents attached thereto, said substituents being selected from the group consisting of alkyl of 1 to 4 carbon atoms, alkoxy of 1 to 4 carbon atoms, alkylthio of 1 to 4 carbon atoms, halogen and trifluoromethyl; a bicyclic aromatic or cycloaliphatic-aromatic ring, especially naphthyl, tetrahydronaphthyl or indanyl; or a mono- or bicyclic heterocyclic ring, especially pyridyl, pyrimidyl, isoquinolyl or thiazolyl;
$R_1$ is

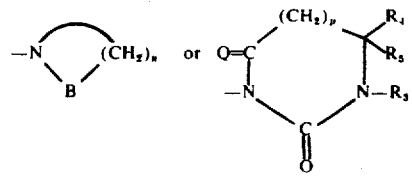

where
B is

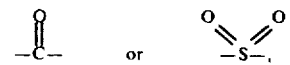

$n$ is 2, 3 or 4,
$R_3$ is hydrogen, alkyl of 1 to 4 carbon atoms or alkanoyl of 1 to 4 carbon atoms,
$R_4$ and $R_5$, which may be identical to or different from each other, are each hydrogen or alkyl of 1 to 4 carbon atoms,
$p$ is 0 or 1, and
Q is oxygen or two hydrogens,
$R_2$ is hydrogen, alkyl of 1 to 4 carbon atoms, alkoxy of 1 to 4 carbon atoms or halogen,
A is a single carbon-to-carbon bond or $-OCH_2-$,
$R_6$ is hydrogen, hydroxyl, alkoxy of 1 to 4 carbon atoms or alkanoyloxy of 1 to 4 carbon atoms, and
$m$ is 0, 1, 2, 3, 4 or 5, but other than 0 when $R_6$ is hydroxyl,
and non-toxic, pharmacologically acceptable acid addition salts thereof; the compounds as well as their salts are useful as CNS-depressants, adrenolytics, antiphologistics, analgesics, antihistamines and anticholesterols.

7 Claims, No Drawings

N-ARYL-N'-(PHENYL-OR PHENOXY-ALKYL)-PIPERAZINES AND SALTS THEREOF

This invention relates to novel N-aryl-N'-(phenyl- or phenoxy-alkyl)-piperazines and non-toxic acid addition salts thereof, as well as to various methods of preparing these compounds.

More particularly, the present invention relates to a novel class of piperazine derivatives represented by the formula

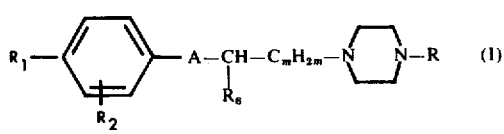
(I)

wherein

R is phenyl; phenyl having one or more substituents attached thereto, said substituents being selected from the group consisting of alkyl of 1 to 4 carbon atoms, alkoxy of 1 to 4 carbon atoms, alkylthio of 1 to 4 carbon atoms, halogen and trifluoromethyl; a bicyclic aromatic or cycloaliphatic-aromatic ring, especially naphthyl, tetrahydronaphthyl or indanyl; or a mono- or bicyclic heterocyclic ring, especially pyridyl, pyrimidyl, isoquinolyl or thiazolyl;

$R_1$ is

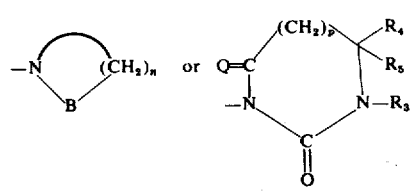

where
B is

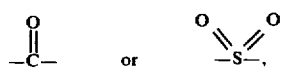

$n$ is 2, 3 or 4,
$R_3$ is hydrogen, alkyl of 1 to 4 carbon atoms or alkanoyl of 1 to 4 carbon atoms,
$R_4$ and $R_5$, which may be identical to or different from each other, are each hydrogen or alkyl of 1 to 4 carbon atoms,
$p$ is 0 or 1, and
Q is oxygen or two hydrogens,
$R_2$ is hydrogen, alkyl of 1 to 4 carbon atoms, alkoxy of 1 to 4 carbon atoms or halogen,
A is a single carbon-to-carbon bond or $-OCH_2-$,
$R_6$ is hydrogen, hydroxyl, alkoxy of 1 to 4 carbon atoms or alkanoyloxy of 1 to 4 carbon atoms, and
$m$ is 0, 1, 2, 3, 4 or 5, but other than 0 when $R_6$ is hydroxyl,
and non-toxic, pharmacologically acceptable acid addition salts thereof.

The hydrocarbon chain represented by $-C_mH_{2m}-$ in formula I may be straight or branched.

The compounds embraced by formula I above may be prepared by the following methods:

Method A

By cyclizing a compound of the formula

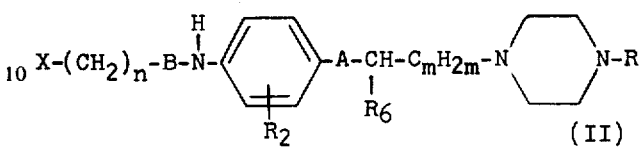
(II)

or

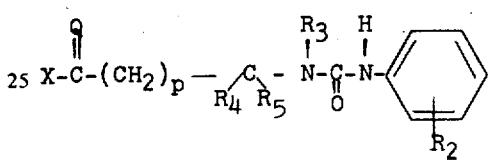

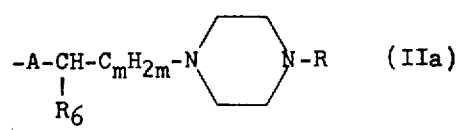
(IIa)

wherein R, $R_2$, $R_3$, $R_6$, A, B, $m$, $n$ and $p$ have the same meanings as in formula I and X is a group which is easily removable as an anion, such as halogen, alkyl or arylsulfonyloxy, or methoxy, when Q is double bonded oxygen, while splitting off HX.

In the case of a compound of the formula II and a compound of the formula IIa wherein Q is two single-bonded hydrogens, the cyclization is effected in the presence of strong or mild alkalies. However, in the case of a compound of the formula IIa, wherein Q is double-bonded oxygen, the cyclization is effected in the presence of an acid, such as hydrochloric acid, sulfuric acid, or hydrobromic acid.

Method B

By reacting a compound of the formula

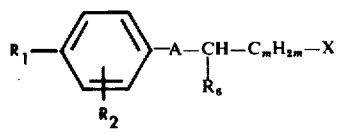
(III)

wherein $R_1$, $R_2$, $R_6$, A and $m$ have the same meanings as in formula I with a compound of the formula

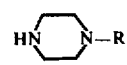
(IV)

wherein R has the same meanings as in formula I, in the presence of HX-binding agent, such as an alkali metal carbonate, potassium tert. butylate, triethylamine or an excess amount of the compound of the formula IV.

Method C

By reductive amination of an oxo-compound of the formula

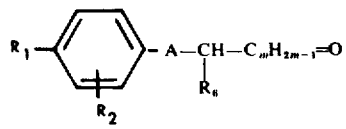   (V)

wherein $R_1$, $R_2$, $R_6$, A and $m$ have the same meanings as in formula I with an amine of the formula IV, for example, in the presence of a metal hydride or catalytically activated hydrogen.

Method D

For the preparation of a compound of the formula I wherein $R_6$ is hydroxyl, by reducing a ketone of the formula

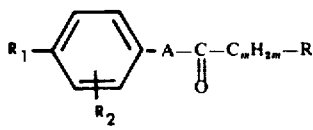   (VI)

wherein R, $R_1$, $R_2$, A and $m$ have the same meanings as in formula I, with a metal hydride or catalytically activated hydrogen.

Method E

For the preparation of a compound of the formula I wherein A is —OCH$_2$— and $R_6$ is hydroxyl, by reacting an oxirane of the formula

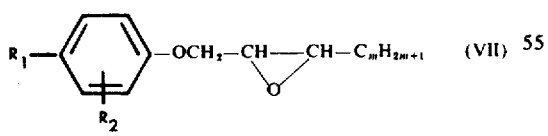   (VII)

wherein $R_1$, $R_2$ and $m$ have the same meanings as in formula I with an amine of the formula IV.

Method F

For the preparation of a compound of the formula I wherein A is —OCH$_2$—, by reacting a phenol of the formula

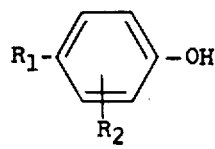   (VIII)

wherein $R_1$ and $R_2$ have the same meanings as in formula I, with a compound of the formula

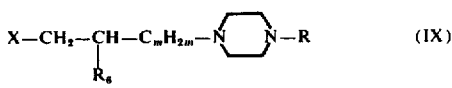   (IX)

wherein X has the same meanings as in formula II and R, and $R_6$ and $m$ have the same meanings as in formula I, in the presence of an HX-binding agent, such as a dilute alkali metal hydroxide or a tertiary amine.

Method G

For the preparation of a compound of the formula I wherein $R_1$ is

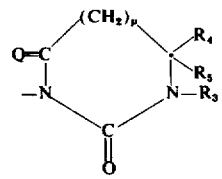

where $R_3$, $R_4$, $R_5$, Q and $p$ have the same meanings as in formula I and $R_6$ is hydrogen, by introducing substituent $R_3$ into a compound of the formula

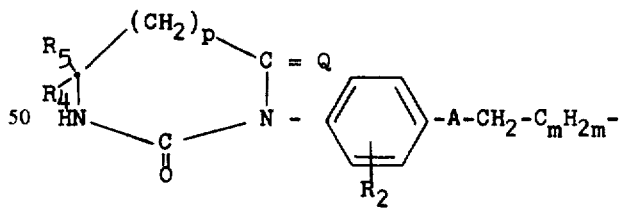

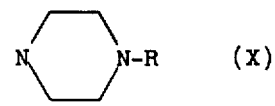   (X)

wherein R, $R_2$, $R_4$, $R_5$, $R_6$, A, Q, $m$ and $p$ have the same meanings as in formula I, with the aid of an alkylating agent or an acylating agent of the formula $R_3 - Y$   (XI)

wherein $R_3$ has the same meanings as in formula I except hydrogen and Y is a group which is removable easily as an anion, such as halogen, alkyl, arylsulfonyloxy, or acyloxy, in the presence of an acid binding agent such as a dilute or concentrated aqueous solution of an alkali metal hydroxide, a tertiary amine or potassium tert. butylate.

Method H

A compound of the formula I, wherein $R_6$ is alkoxy of 1 to 4 carbon atoms or alkanoyloxy of 1 to 4 carbon atoms, may also be prepared in the following manner: By introducing substituent $R_6$ into a compound of the formula

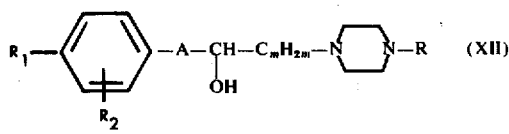

wherein R, $R_1$, $R_2$, A and m have the same meanings as in formula I, by means of an alkylating agent or an acylating agent of the formula $$R_6' - Y \qquad (XIII)$$

wherein $R_6'$ means alkyl or alkanoyl of 1 to 4 carbon atomes, and Y has the same meanings as in formula XI. If the reaction is an alkylation, it is appropriately carried out in the presence of an alkali metal containing compound such as NaH, NaNH$_2$, potassium tert.-butylate or a sodium dispersion. If the reaction is an acylation, it is appropriately conducted in the presence of an acid binding agent, such as an alkali metal carbonate or a tertiary amine.

Method I

A compound of the formula I wherein $R_1$ is

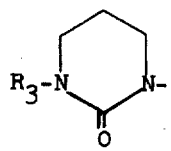

may be prepared by reacting a diamine of the formula

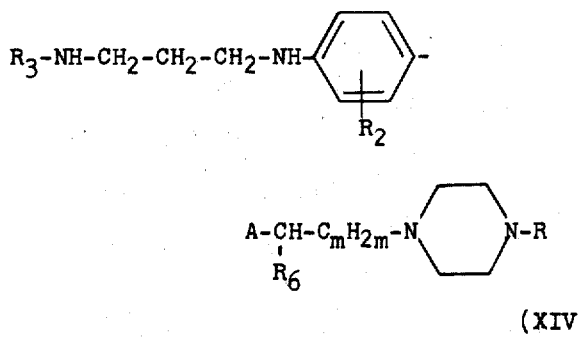

wherein R, $R_2$, $R_3$ and $R_6$, A and m have the same meanings as in formula I, with a reactive carbonic acid derivative, such as phosgene, N,N-carbonyl- diimidazole, a chlorocarbonate, a carbonate or a metal cyanate, in the presence of an acid. Intermediate products formed thereby, such as carbamates, ureas and carbamic acid chlorides, may optionally be isolated and used for cyclization.

Method J

A compound of the formula I, wherein $R_6$ is hydrogen, may also be prepared by reducing a compound of the formula

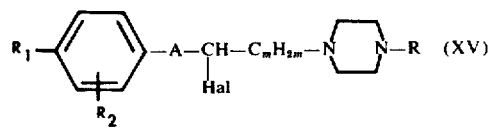

wherein R, $R_1$, $R_2$, A and m have the same meanings as in formula I, and Hal is chloride, bromide or iodide, with catalytically activated hydrogen.

The starting compounds for Methods A to J are either known or may be prepared according to known methods.

For example, the compounds of the formula II may be prepared by reacting a nitro compound of the formula

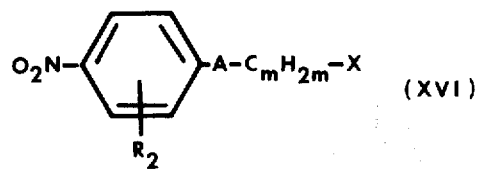

wherein $R_2$, A, and m have the same meanings as in formula I and X has the same meanings as in formula II, with a piperazine of the formula IV. Subsequently, the nitro group is catalytically reduced to an amino group and the resulting compound of the formula

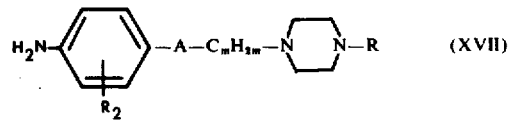

wherein R, $R_2$, A and m have the same meanings as in formula I is reacted with, for example, an ω-chloroacylchloride, a 3-chloropropylisocyanate or a ω-isocyanate-alkyl carboxylate to produce a compound of the formula II or IIa in which $R_6$ is hydrogen.

Intermediate compounds of the formula III are prepared by reacting 4-amino-phenyl-ethylacetate with an ω-chloroacylchloride, a 3-chloropropylisocyanate or an ω-isocyanatoalkylcarboxylate to produce a compound of the formula

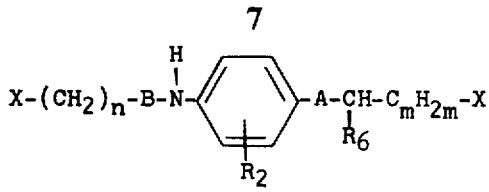

(XVIII)

or

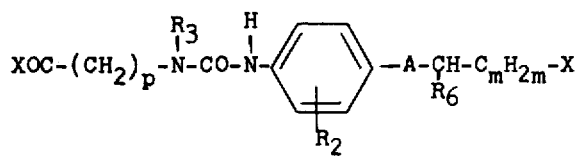

(XVIII a)

wherein $R_2$, $R_3$, $R_6$, A, B, m, n and p have the same meanings as in formula I and X has the same meanings as in formula II, which is then cyclized to produce a compound of the formula III.

Compounds of the formula V are produced by reducing a compound of the formula

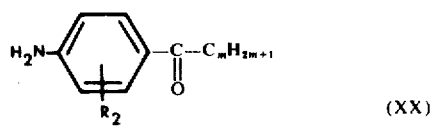

(XIX)

wherein $R_2$, $R_6$, A and m have the same meanings as in formula I, preferably with catalytically activated hydrogen. The corresponding amino compound is thereby produced which is then reacted with an ω-chloroacylchloride, a 3-chloropropylisocyanate or an ω-isocyanatoalkylcarbonxylate. Subsequent cyclization produces a compound of the formula V.

Compounds of formula VI are prepared by reacting an aminoketone of the formula

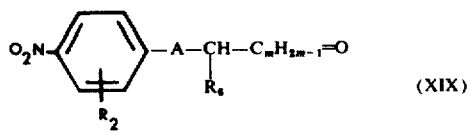

(XX)

wherein $R_2$ and m have the same meanings as in formula I, with an ω-chloropropylisocyanate or an ω-isocyanatoalkylcarboxylate, and subsequently cyclizing the reaction product to produce a compound of the formula

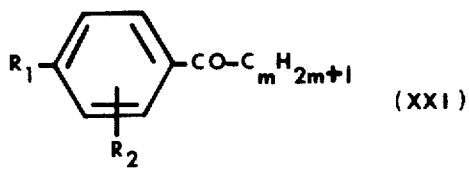

(XXI)

wherein $R_1$, $R_2$ and m have the same meanings as in formula I.

Subsequently, the cyclization product is brominated to produce the corresponding α-bromoketone, and the latter is reacted with an amine of the formula IV to produce a compound of the formula VI.

The oxiranes of the formula VII are produced by reacting a correspondingly substituted benzyloxyaniline with an ω-chloroacylchloride, 3-chloropropylisocyanate or an ω-isocyanatoalkylcarboxylate, and then cyclizing the reaction product to produce compound of formula

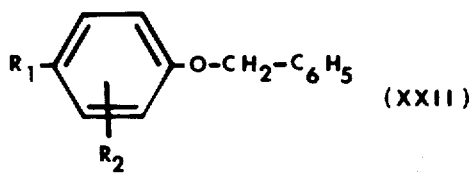

(XXII)

wherein $R_1$ and $R_2$ have the same meanings as in formula I. By means of catalytic debenzylation and reaction with an oxirane of the formula $$X-CH_2-CH\underset{O}{-\!-\!-}CH-C_mH_{2m+1} \quad (XXIII)$$

wherein m has the same meanings as in formula I and X has the same meanings as in formula II, a compound of the formula VII is obtained.

The starting compounds of the formula VIII are obtained as intermediates in Method E.

Compounds of the formula X are obtained in the course of Method A.

Compounds of the formula XII are obtained in the course of Methods D and E.

Compounds of the formula XIV are prepared by reacting an amino compound obtained in accordance with Method A with acrylonitrile, and reducing the compound thus obtained into a compound of the formula XIV.

In order to prepare compounds of formula XV, an alcohol resulting from Method D or E, is reacted with phosphorus pentachloride or thionylchloride.

If $R_6$ is other than hydrogen or if $C_mH_{2m}$ is branched, the compounds embraced by formula I possess an asymmetric carbon atom and occur, therefore, in the form of a racemic mixture or of optically active antipodes. The optically active antipode compounds may be obtained either by starting from optically active starting materials or by converting the obtained racemates by means of optically active auxiliary acids, for example, dibenzoyl-D-tartaric acid, di-p-toluyl-D-tartaric acid or D-3-bromocamphor-8-sulfonic acid, into the diastereomeric salts which are separated by fractional precipitation or fractional crystallization. If $R_6$ is other than hydrogen and if $C_mH_{2m}$ is branched as well, then threo-isomers and erythro-isomers will also occur.

The compounds embraced by formula I are organic bases and therefore form acid addition salts with inorganic or organic acids, by known methods. Examples of non-toxic, pharmacologically acceptable acid addition salts are those formed with hydrochloric acid, hydrobromic acid, sulfuric acid, methanesulfonic acid, succinic acid, tartaric acid, 8-chlorotheophylline or the like.

The following examples further illustrate the present invention and will enable others skilled in the art to understand it more completely. It should be understood, however, that the invention is not limited solely to the particular examples given below.

EXAMPLE 1

N-[4-(1'-Pyrrolidin-2'-one-yl)-phenethyl]-N'-(2'',3''-xylyl)piperazine and its methanesulfonate by Method A a) 7.73 gm (25 millimols) of N-(p-amino-phenethyl)-N'-(2,3-xylyl)-piperazine were dissolved in 80 ml of acetonitrile, 6.9 gm (50 millimols) of potassium carbonate were added to the solution, and then, while stirring, 4.18 gm (30 millimols) of 4-chlorobutyric acid chloride were added dropwise. Thereafter, the mixture was allowed to react for two more hours, and was then cooled and vacuum-filtered, yielding as the filter cake 63% of theory of N-[p-(4-chlorobutyramido)-phenethyl]-N'-(2',3'-xylyl)-piperazine, m.p. 136°C.

b) 6.5 gm (15.8 millimols) of the product obtained in a) were admixed 1.05 gm (18 millimols) of caustic alkali and 30 ml of ethanol, and the mixture was refluxed for one hour. Thereafter, the reaction mixture was cooled, vacuum-filtered, and the filter cake was rinsed with cold water and then dried. The dry substance, the free base N-[4-(1'-pyrrolidin-2'-one-yl)-phenethyl]-N'-(2'',3''-xylyl)-piperazine, m.p. 159°–160°C, was dissolved in ethanol, and methanesulfonic acid was added to the solution, whereupon the methanesulfonate, m.p. 222°C, of the formula

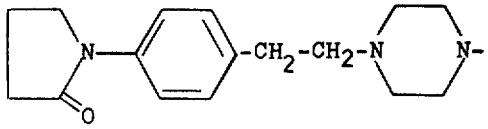

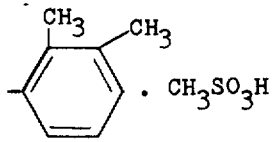

precipitated out.

EXAMPLE 2

N-[p-(1-Hexahydropyrimidin-2-one-yl)-phenethyl]-N'-(m-tolyl)-piperazine and its methanesulfonate by Method A a) 11.3 gm (38.5 millimols) of N-(p-amino-phenethyl)-N'-(m-tolyl)-piperazine, 4.6 gm (38.5 millimols) of 3-chloropropyl-isocyanate and 120 ml of toluene were admixed with each other, accompanied by gentle agitation, and the mixture was allowed to react for two hours and was then vacuum-filtered, yielding as the filter cake 90% of theory of N-[p-(3-chloropropyl-ureido)-phenethyl]-N'-(m-tolyl)-piperazine, m.p. 168°C.

b) The product obtained in a) was dissolved in ethanol, an equimolar amount of caustic alkali was added to the solution, and the mixture was refluxed for 15 minutes. Thereafter, the reaction mixture was cooled, vacuum-filtered, and the filter cake was rinsed with water and dried, yielding the free base N-[p-(1-hexahydropyrimidin-2-one-yl)-phenethyl]-N'-(m-tolyl)-piperazine, m.p. 213°C. The base was dissolved in ethanol, and upon addition of methanesulfonic acid the methanesulfonate, m.p. 251°–252°C, of the formula

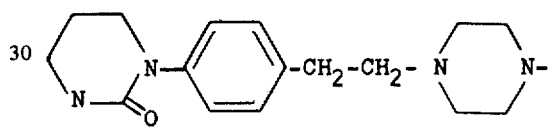

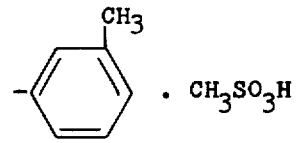

precipitated out.

EXAMPLE 3

N-[p-(1-Imidazolidin-2,5-dione-yl)-phenethyl]-N'-(β-indanyl)-piperazine and its methanesulfonate by Method A a) 8.0 gm (25 millimols) of N-(p-amino-phenethyl)-N'-(β-indanyl)-piperazine were dissolved in 80 ml of toluene, the solution was admixed with 2.88 gm (25 millimols) of methyl isocyanato-acetate, and the mixture was allowed to react for two hours. Thereafter, the reaction mixture was vacuum-filtered, and the filter cake was dried, yielding the reaction product which had a melting point of 188°C.

b) 10 gm of the product obtained in a) were admixed with 25 ml of aqueous semi-concentrated hydrochloric acid, and, while stirring, the mixture was heated on a boiling water bath and then cooled and vacuum-filtered. The filter cake was suspended in water, and upon addition of ammonia the free base N-[p-(1-imidazolidin-2,5-dione-yl)-phenethyl]-N'-(β-indanyl)-piperazine, m.p. 214°C, separated out. The base was dissolved in hot ethanol, the calculated amount of methanesulfonic acid was added to the hot solution, and upon cooling, the methanesulfonate, m.p. 308° – 310°C, of the formula

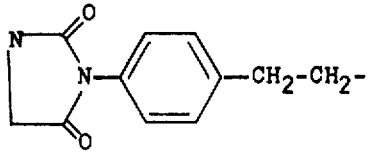

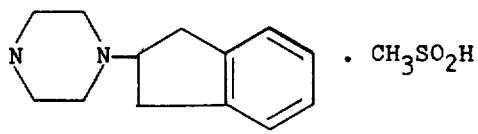

separated out.

EXAMPLE 4

N-[p-(2-Isothiazolidin-1,1-dioxide-yl)-phenethyl]-N'-(2'-pyridyl)-piperazine and its methanesulfonate by Method A.

7.05 gm (25 millimols) of N-(p-amino-phenethyl)-N'-(2-pyridyl)-piperazine were dissolved in 100 ml of acetonitrile. 6.9 gm (50 millimols) of potassium carbonate were added to the solution, and then, while stirring the mixture, 5.4 gm (30 millimols) of 3-chloro-propyl-sulfochloride were added, and the mixture was allowed to stand at room temperature for two hours. Thereafter, the reaction mixture was briefly heated to the boiling point, then cooled, 200 ml of water were added, and the mixture was extracted with ethyl acetate. The organic phase was dried with sodium sulfate, the solvent was distilled off in vacuo, the residue (9 gm) was dissolved in 90 ml of ethanol, an equimolar amount of caustic alkali was added, and the resulting mixture was refluxed for 2 hours. Thereafter, the reaction mixture was cooled, vacuum-filtered, and the filter cake was dried, yielding the free base N-[p-(2-isothiazolidin-1,1-dioxide-yl)-phenethyl]-N'-(2'-pyridyl)-piperazine, m.p. 133° – 134°C. The base was dissolved in ethanol, and the solution was admixed with the calculated amount of methanesulfonic acid, whereby the methanesulfonate, m.p. 213° – 214°C, of the formula

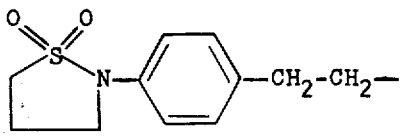

separated out.

EXAMPLE 5

Using a procedure analogous to that described in Example 1, N-[p-(1-piperidin-2-one-yl)-phenethyl]-N'-(o-tolyl)-piperazine, m.p. 115°–117°C, was prepared from 7.37 gm (25 mmol) of N-(p-amino-phenethyl)-N'-(o-tolyl)-piperazine, 6.9 gm (50 mmol) of potassium carbonate, 4.64 gm (30 mmol) of 5-chloro-valeric acid chloride in 75 ml of acetonitrile, via the 5-chlorovalerylanilide derivative, m.p. 109°-110°C. Its hydrochloride had a melting point of 308°C.

EXAMPLE 6

Using a procedure analogous to that described in Example 3, N-[p-(1-(4-methyl)-imidazolidin-2,5-dione-yl)-phenethyl]-N'-(α-naphthyl)-piperazine, was prepared from N-(p-amino-phenethyl)-N'-(α-naphthyl)-piperazine and 2-isocyanato-propionic acid methyl ester. Its hydrochloride had a melting point of 315°C.

EXAMPLE 7

Using a procedure analogous to that described in Example 3, N-[p-(1-(4,4-dimethyl)-imidazolidin-2,5-dione-yl)-α-methyl-phenethyl]-N'-(p-chlorophenyl)-piperazine was prepard from N-(p-aminophenethyl-α-methyl)-N'-(p-chlorophenyl)-piperazine and 2-isocyanato-2-methyl-propionic acid methyl ester. Its hydrochloride had a melting point of 316°-318°C.

EXAMPLE 8

Using a procedure analogous to that described in Example 4, N-[p-(2-tetrahydro-1,2-thiazin-1,1-dioxide-yl)-phenethyl]-N'-(o-tolyl)-piperazine, was prepared from N-(p-aminophenethyl)-N'-(o-tolyl)-piperazine and 4-chlorobutanesulfonic acid chloride. Its hydrochloride had a melting point of 250°C.

EXAMPLE 9

N-[p-(2-Isothiazolidin-1,1-dioxide-yl)-α-methyl-phenethyl]-N'-(o-tolyl)-piperazine and its hydrochloride by Method C 11.6 gm (46 millimols) of p-(2'-isothiazolidin-1,1-dioxide-yl)-phenyl-acetone and 8.1 gm (46 millimols) of N-(o-tolyl)-piperazine were dissolved in 100 ml of methanol, 1 gm of platinum was added, and the mixture was hydrogenated at 60°C and elevated pressure until the absorption of hydrogen had ceased. The catalyst was now filtered off, the solvent was distilled out of the filtrate in vacuo, and the residue, the free base N-[p-(2-isothiazolidin-1,1-dioxide-yl)-α-methyl-phenethyl]-N'-(o-tolyl)-piperazine, was dissolved in a little methanol. The calculated amount of 2N hydrochloric acid was added to the solution, and the mixture was cooled and vacuum-filtered. The filter cake was the hydrochloride, m.p. 269°-272°C of the formula

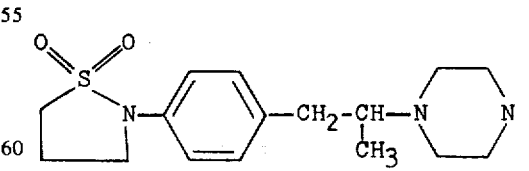

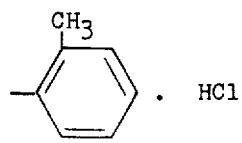

EXAMPLE 10

N-[-p-(1-Hexahydropyrimidin-2-one-yl)-β-hydroxyphenethyl]-N'-(o-tolyl)-piperazine and its hydrochloride by Method D 14.0 gm (35.7 millimols) of 4'-(1-hexahydropyrimidin-2-one-yl)-β-(N'-o-tolyl-piperazino)-acetophenone were dissolved in methanol, 2.71 gm (71.4 millimols) of sodium borohydride were added in small portions to the solution, and the resulting mixture was stirred at room temperature for 12 hours. Thereafter, the reaction mixture was made acid with glacial acetic acid, then made alkaline again with ammonia, vacuum-filtered, and the filter cake was dried, yielding the free base N-[p-(1-hexahydropyrimidin-2-one-yl)-β-hydroxy-phenethyl]-N'-(o-tolyl)-piperazine, m.p. 234° – 235°C. The base was suspended in acetonitrile, and the suspension was acidified with ethereal hydrochloric acid, yielding the hydrochloride, m.p. 249°C, of the formula

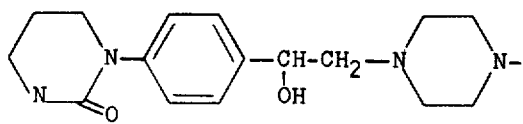

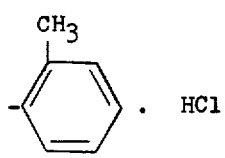

EXAMPLE 11

N-[p-(1-Pyrrolidin-2-one-yl)-phenoxyethyl]-N'-(o-tolyl)-piperazine and its hydrochloride by Method F 8.85 gm (50 millimols) of p-(1-pyrrolidin-2-one-yl)-phenyl — obtained by reacting p-benzyloxy-aniline with 4-chloro-butyric acid chloride, HCl-elimination and subsequent catalytic debenzylation — were admixed with 100 ml of acetonitrile, 13.8 gm of potassium carbonate, 11.9 gm (50 millimols) of N-(β-chloro-ethyl)-N'-(o-tolyl)-piperazine and 8.8 gm (50 millimols) of N-(o-tolyl)-piperazine, and the mixture was refluxed for 3 hours. Thereafter, the reaction mixture was cooled, vacuum-filtered, and the solvent was distilled out of the filtrate in vacuo. The residue, the free base N-[p-(1pyrrolidin-2-one-yl)-phenoxyethyl]-N'-(o-tolyl)-piperazine, was dissolved in a little methanol, the resulting solution was made acid with dilute hydrochloric acid, water was added, and the precipitate formed thereby was collected and recrystallized from ethanol, yielding the hydrochloride, m.p. 242°C, of the formula

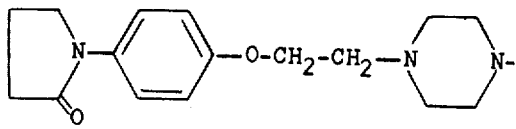

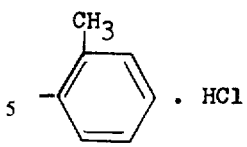

EXAMPLE 12

N-[p-(3-Acetyl-1-imidazolidin-2,5-dione-yl)-phenethyl]-N'-(o-tolyl)-piperazine and its methanesulfonate by Method G A mixture consisting of 7.3 gm (19.3 millimols) of N-[p-(1-imidazolidin-2,5-dione-yl)-phenethyl]-N'-(o-tolyl)-piperazine (m.p. 174°–175°C) and 15 ml of acetic acid anhydride was heated for 90 minutes at 120°–130°C. Thereafter, the reaction mixture was poured into water, and the aqueous solution was made weakly alkaline with potassium carbonate, whereupon a crystalline substance separated out slowly which was collected by vacuum filtration and recrystallized from ethanol, yielding the free base, m.p. 148° – 149°C, of the formula

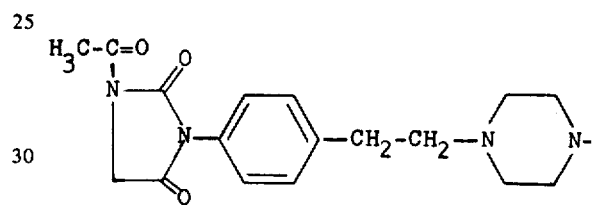

The base was dissolved in ethanol, the calculated amount of methanesulfonic acid was added to the solution, and the precipitate formed thereby was collected, yielding the methanesulfonate of the base, which had a melting point of 201° – 202°C.

EXAMPLE 13

1-[p-(2'-Isothiazolidin-1', 1'-dioxide-yl)-phenyl]-2-[N'-(2'', 4''-xylyl)-piperazine]-ethyl butyrate and its methanesulfonate by Method H A mixture consisting of 10.3 gm (24 millimols) of N-[p-(2-isothiazolidin-1,1-dioxide-yl)-β-hydroxyphenethyl]-N'-(2',4'-xylyl)-piperazine (m.p. 177°C) and 50 ml of butyric acid anhydride was heated for one hour at 140° – 150°C, while stirring. Thereafter, the resulting clear, brown solution was evaporated to dryness in vacuo, the partially crystalline residue was stirred with a little ethanol, the mixture was vacuum-filtered, and the filter cake was dried, yielding the free base, m.p. 160°C, of the formula

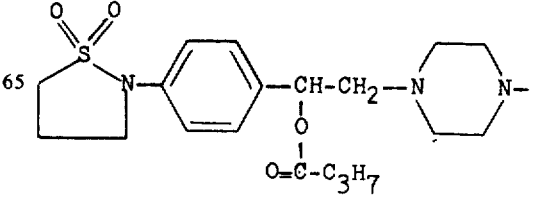

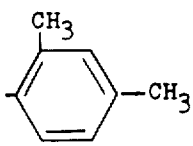

The base was suspended in hot ethanol, the suspension was admixed with the calculated amount of methanesulfonic acid, the resulting clear solution was cooled, and the substance precipitated thereby was collected by vacuum filtration, yielding the methanesulfonate of the base, which had a melting point of 195°C.

EXAMPLE 14

N-[p-(1-Hexahydropyrimidin-2-one-yl)-phenethyl]-N'-(o-tolyl)-piperazine by Method J 7.9 gm (20 millimols) of N-[p-(1-hexahydropyrimidin-2-one-yl)-β-hydroxy-phenethyl]-N'-(o-tolyl)-piperazine (see Example 10) were dissolved in 100 ml of acetonitrile, and, while stirring and cooling the solution, 8.34 gm (40 millimols) of phosphorus pentachloride were added thereto. A good yield of N-[p-(1-hexahydropyrimidin-2-one-yl)-β-chlorophenethyl]-N'-(o-tolyl)-piperazine dihydrochloride was obtained. This product was dissolved in 100 ml of methanol, 10 gm of dimethylaniline and a small amount of Raney nickel were added to the solution, and the mixture was hyhdrogenated at atmospheric pressure, yielding N-[p-(1-hexahydropyrimidin-2-one-yl)-phenethyl]-N'-(o-tolyl)-piperazine, m.p. 127° - 128°C, after working up the reaction mixture in conventional manner.

EXAMPLE 15

N-[p-(1-Pyrrolidin-2-one-yl)-phenethyl]-N'-(o-chloro-phenyl)-piperazine and its methanesulfonate by Method B.

a) 17.9 gm (0.1 mol) of p-aminophenethyl acetate were dissolved in 180 ml of acetonitrile, 27.6 gm (0.2 mol) of potassium carbonate were added to the solution, and then, while stirring, 17.0 gm (0.12 mol) of 4-chlorobutyric acid chloride were added dropwise. The resulting mixture was stirred for 2 hours at room temperature, thereafter heated to 50°C and then vacuum-filtered to remove precipitated inorganic salts. The solvent was distilled out of the filtrate in vacuo, and the residue was recrystallized from isopropanol, yielding 14.8 gm (52.2% of theory) of p-(4-chlorobutyramido)-phenethyl acetate, m.p. 83°C.

b) 28.4 gm (0.1 mol) of the end product obtained in a) were dissolved in 200 ml of methanol, a solution of 13.4 gm (0.24 mol) of potassium hydroxide in 100 ml of water was added, and the mixture was refluxed for 1 hour. Thereafter, the solvent was distilled off in vacuo, the residue was taken up in methylene chloride, the solution was extracted once with water, the organic phase was dried with sodium sulfate, and the solvent was then distilled off in vacuo. The residue was recrystallized from isopropanol, yielding 12.4 gm (60.5% of theory) of p-(1-pyrrolidin-2-one-yl)-phenethanol, m.p. 96°C.

c) 10.25 gm (0.05 mol) of the product obtained in b) were dissolved in 50 ml of dry pyridine, and, while stirring the solution at 15° - 20°C, 6.9 gm (0.06 mol) of methane-sulfonic acid chloride were added. The resulting mixture was stirred for 2 hours more at room temperature and was then poured over ice water. The aqueous mixture was vacuum-filtered, and the crystalline filter cake was recrystallized from methanol, yielding 6.5 gm (46% of theory) of p-(1-pyrrolidin-2-one-yl)-phenethyl methanesulfonate, m.p. 94°C.

d) 5.66 gm (20 millimols) of the product obtained in c) were admixed with 3.93 gm (20 millimols) of N-(o-chloro-phenyl)-piperazine, 5.5 gm (40 millimols) of potassium carbonate and 50 ml of acetonitrile, and the mixture was refluxed for five hours. Thereafter, while still hot, the reaction mixture was vacuum-filtered to remove the precipitated inorganic salts, the filtrate was cooled on an ice-salt bath, and the precipitate formed thereby was collected by vacuum filtration and dried, yielding the free base N-[p-(1-pyrrolidin-2-one-yl)-phenethyl]-N'-(o-chloro-phenyl)-piperazine, m.p. 132°C.

The base was dissolved in hot ethanol, the calculated amount of methanesulfonic acid was added to the hot solution, the mixture was cooled, and the precipitate formed thereby was collected and dried, yieding 6.6 gm (68.8% of theory) of the methanesulfonate, m.p. 201°C.

EXAMPLE 16

N-(γ-[p-(1-Hexahydropyrimidin-2-one-yl)-phenyl]-n-propyl)-N'-phenyl-piperazine by Method I a) A mixture consisting of 29.5 gm (0.1 mol) of N-[γ-(p-amino-phenyl)-n-propyl]-N'-phenyl-piperazine (m.p. 102°C), 5.8 gm (0.11 mol) of acetonitrile and 20 ml of glacial acetic acid was refluxed for 20 hours. Thereafter, the solvent was distilled off in vacuo, and the residue was recyrstallized from dilute methanol, yielding 28.3 gm (81.3% of theory) of N-[γ-(p-[β-cyanoethyl-amino]-phenyl)-n-propyl]-N'-phenyl-piperazine, m.p. 141° - 143°C.

b) 20.9 gm (0.06 mol) of the product obtained in a) were hydrogenated in methanol in the presence of platinum oxide as a catalyst, yielding 19.5 gm (92.2% of theory) of the corresponding diamine, i.e. N-[3-(p-[γ-amino-n-propyl]-amino-phenyl)-n-propyl]-N'-phenyl-piperazine.

c) 17.6 gm (0.05 mol) of the product obtained in b) were dissolved in 200 ml of absolute benzene, the solution was admixed with a solution of 8.9 gm (0.055 mol) of N,N'-carbonyl-diimidazole in 50 ml of absolute benzene, and the mixture was allowed to stand overnight at room temperature and was then refluxed for two hours. Thereafter, the solvent was distilled off in vacuo, and the residue was recrystallized twice from isopropanol, yielding the compound of the formula

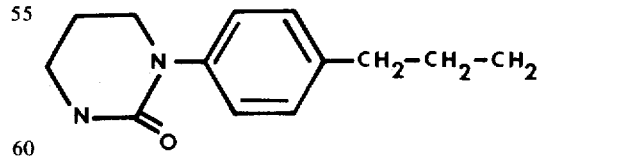

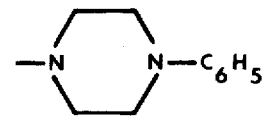

which had a melting ponit of 120° - 122°C.

EXAMPLE 17

N-[β-Hydroxy-γ-(p-[1-pyrrolidin-2-one-yl]-phenoxy)-n-propyl]-N'-phenyl-piperazine and its hydrochloride by Method E a) 17.7 gm (0.1 mol) of p-(1-pyrrolidin-2-one-yl)-phenol (see Example 11) were dissolved in 200 ml of 0.05N potassium hydroxide, and, while stirring and cooling the solution in ice water, 10.2 gm (0.11 mol) of epichlorohydrin were added dropwise thereto. The resulting mixture was stirred for 20 hours more at room temperature, then heated for 30 minutes at 50°C, cooled, and extracted with chloroform. The organic phase wsa extracted with 1N potassium hydroxide, dried over sodium sulfate, the solvent was distilled off in vacuo, and the residue was recrystallized from dilute methanol, yielding 14.8 gm (63.5% of theory) of 3-[p-(1'-pyrrolidin-2'-one-yl)-phenoxy]-propyleneoxide, m.p. 164° – 165°C.

b) A mixture consisting of 11.8 gm (0.05 mol) of the product obtained in a), 8.1 gm (0.05 mol) of N-phenyl-piperazine and 100 ml of acetonitrile was refluxed for 6 hours. Thereafter, the solvent was distilled off in vacuo, the calculated amount of ethanolic hydrochloric acid was added to the residue, and upon further addition of ethanol the hydrochloride, m.p. 210° – 212°C, of the formula

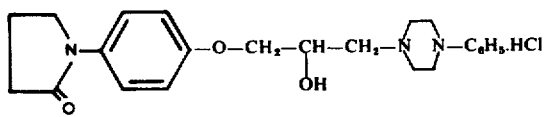

crystallized out. The yield was 45% of theory.

The following compounds according to the invention were prepared using procedures analogous to the methods previously described.

TABLE 1

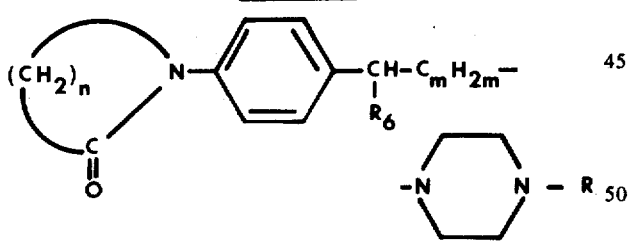

| Ex.No. | n | $R_5$ | $C_mH_{2m}$ | R | M.p. °C |
|---|---|---|---|---|---|
| 18 | 3 | H | —$CH_2$— | o-Tolyl | 210–211* |
| 19 | 3 | H | $CH_3$<br>$\|$<br>—CH— | o-Tolyl | 208–209** |
| 20 | 3 | H | —$CH_2$— | p-Tolyl | 195–196* |
| 21 | 3 | H | —$CH_2$— | α-Naphthyl | 220–221* |
| 22 | 3 | H | —$CH_2$— | m-Tolyl | 222* |
| 23 | 3 | H | —$CH_2$— | 2-n-Butoxyphenyl | 137–138* |
| 24 | 3 | —OH | —$CH_2$— | Phenyl | 189–190* |
| 25 | 4 | H | —$CH_2$— | Phenyl | 235–236* |
| 26 | 4 | H | —$CH_2$— |  | 141–146* |
| 27 | 3 | —OAc | —$CH_2$— | Phenyl | 218–219* |
| 28 | 3 | H | — | 2,4-Xylyl | 119–120 |
| 29 | 3 | H | —$CH_2$—$CH_2$— | Phenyl | 157–158* |

*methanesulfonate
**hydrochloride

TABLE 2

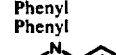

| Ex.No. | $R_6$ | $C_mH_{2m}$ | R | M.p. °C |
|---|---|---|---|---|
| 30 | H | $CH_3$<br>$\|$<br>—CH— | o-Tolyl | 225–226* |
| 31 | H | —$CH_2$— | 4-Chlorphenyl | 233* |
| 32 | H | —$CH_2$— | 3,4-Xylyl | 250* |
| 33 | H | —$CH_2$— | 2,4-Xylyl | 200* |
| 34 | H | —$CH_2$— | 2,3-Xylyl | 199* |
| 35 | H | —$CH_2$— | α-Naphthyl | 238–239* |
| 36 | H | —$CH_2$— | 2-Isopropylphenyl | 168* |
| 37 | H | —$CH_2$— | Phenyl | 175–176* |
| 38 | H | —$CH_2$— | 2-Methoxyphenyl | 213 |
| 39 | H | — | α-Naphthyl | 230–231* |

*methanesulfonate

TABLE 3

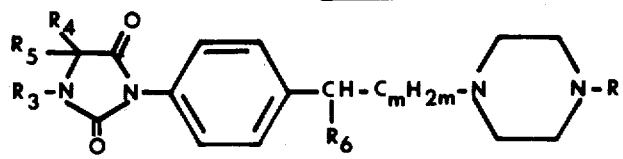

| Ex. No. | $R_6$ | $C_mH_{2m}$ | R | $R_3$ | $R_4$ and $R_5$ | M.p. °C |
|---|---|---|---|---|---|---|
| 40 | H | —$CH_2$— | o-Tolyl | H | H | 227–228* |
| 41 | H | $CH_3$<br>$\|$<br>—CH— | o-Tolyl | H | H | 295–296** |
| 42 | H | —$CH_2$— | 2-Chlorphenyl | H | H | 268–271** |
| 43 | H | —$CH_2$— | 2,4-Xylyl | H | H | 214* |
| 44 | H | —$CH_2$— | β-Naphthyl | H | H | 277–278* |
| 45 | H | —$CH_2$— | Phenyl | H | H | 255–256* |

| Ex. No. | R₆ | CₘH₂ₘ | R | R₃ | R₄ and R₅ | M.p. °C |
|---|---|---|---|---|---|---|
| 46 | H | —CH₂— | 2-pyrimidinyl | H | H | 258–259* |
| 47 | H | —CH₂— | 2-Methoxy-phenyl | H | H | 210–211* |
| 48 | H | —CH₂— | 2-quinolinyl | H | H | 271–273*** |
| 49 | H | —CH₂— | 2-pyridyl | H | H | 203–205* |
| 50 | H | — | Phenyl | H | H | 190–191* |
| 51 | H | —CH₂— | α-Naphthyl | H | H | 277–278* |
| 52 | H | —CH₂— | o-Tolyl | H | R₄=CH₃ R₅=CH₃ | 205–206* |
| 53 | H | —CH₂—CH₂— | Phenyl | H | H | 207* |
| 54 | H | —CH₂— | 2-thiazolyl | H | H | 267–268** |
| 55 | H | —CH₂— | 2-n-Butylthio-phenyl | H | H | 195–196* |
| 56 | H | —CH₂— | 2-Methylthio-phenyl | H | H | 216–217* |

*methanesulfonate
**hydrochloride
***di(methanesulfonate)

TABLE 4

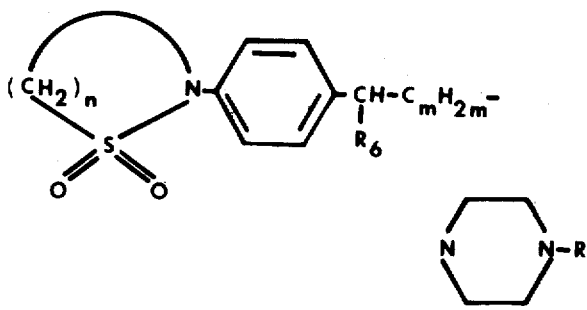

| Ex. No. | n | R₆ | CₘH₂ₘ | R | M.p. °C |
|---|---|---|---|---|---|
| 57 | 3 | H | —CH₂— | o-Tolyl | 191–193* |
| 58 | 3 | H | —CH₂— | 3,4-Xylyl | 224–225** |
| 59 | 3 | H | —CH₂— | 2,3-Xylyl | 225–226* |
| 60 | 3 | H | —CH₂— | β-Indanyl | 224–226* |
| 61 | 3 | H | —CH₂— | 2-Chlor-phenyl | 221–223* |
| 62 | 3 | H | —CH₂— | 2-Isopropyl-phenyl | 224–225* |
| 63 | 3 | H | —CH₂— | α-Naphthyl | 212–213* |
| 64 | 3 | H | —CH₂— | Phenyl | 256–257* |
| 65 | 3 | H | —CH₂— | 2-pyrimidinyl | 168* |
| 66 | 3 | H | —CH₂— | 2-n-Butoxy-phenyl | 135–136* |
| 67 | 3 | H | —CH₂— | tetrahydronaphthyl | 235–236* |
| 68 | 3 | H | —CH₂— | 2,4-Xylyl | 187* |
| 69 | 3 | O—C(=O)—C₃H₇ | —CH₂— | 2,4-Xylyl | 195* |
| 70 | 3 | H | — | o-Tolyl | 266–268** |
| 71 | 3 | H | —CH(CH₃)— | α-Naphthyl | 277–278* |
| 72 | 3 | H | —CH₂— | 2-n-Butyl-thiophenyl | 165–166* |
| 73 | 3 | H | —CH₂— | 2-Methyl-thiophenyl | 211–212* |
| 74 | 4 | H | —CH₂— | o-Tolyl | 250** |

*methanesulfonate
**hydrochloride

The compounds of the present invention, that is, those embraced by formula I above and their non-toxic, pharmacologically acceptable acid addition salts, have useful pharmacodynamic properties. More particularly, they exhibit CNS-depressing, adrenolytic, as well as antihistaminic, anticholesterol, antiphlogistic and analgesic activities in warmblooded animals, such as mice, rats, dogs and cats, and very low toxicites.

By virtue of their CNS-depressing activities, whch are significantly superior to those of related compounds disclosed in German Auslegeschrift No. 1,189,553, the compounds of the instant invention are useful as sedatives neuroleptics and tranquilizers.

On account of their adrenolytic activities, the compounds of this invention are useful as hypotensives and bronchospasmolytics.

A sub-genus of particularly effective CNS-depressants is constituted by those compounds of the formula I wherein R is o- and/or m-substituted phenyl, such as N-[p-(1-hexahydropyrimidin-2-one-yl)-phenethyl]-N'-(m-tolyl)-piperazine,
N-[p-(1-pyrrolidin-2-one-yl)-phenethyl]-N'-(2',3'-xylyl)-piperazine,
N-[p-(1-pyridin-2-one-yl)-phenethyl]-N'-(o-tolyl)-piperazine,
N-[p-(2-isothiazolidin-1,1-dioxide-yl)-phenethyl]-N'-(2',3'-xylyl)-piperazine, and
N-[p-(2-tetrahydro-1,2-thiazin-1,1-dioxide-yl)-phenethyl]-N'-(o-tolyl)-piperazine, and their non-toxic, pharmacologically acceptable acid addition salts.

Another sub-genus of very effective compounds is constituted by those of the formula I wherein R, is 1-imidazolidin-2,5-dione-yl, such as N-[p-(1-imidazolidin-2,5-dione-yl)-phenethyl]-N'-(β-indanyl)-piperazine,
N-[p-(1-imidazolidin-2,5-dione-yl)-phenethyl]-N'-phenyl-piperazine, and
N-[p-(1-imidazolidin-2,5-dione-yl)-phenethyl]-N'-(o-chloro-phenyl)-piperazine, and their non-toxic, pharmacologically acceptable acid addition salts.

Still another sub-genus is constituted by N-[p-(2-isothiazolidin-1,1-dioxide-yl)-phenethyl]-N'-(2'-pyridyl)-piperazine and non-toxic, pharmacologically acceptable acid addition salts thereof, which are particularly effective.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.016 to 1.67 mgm/kg body weight, preferably 0.083 to 0.83 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 75

Tablets

The tablet composition was compounded from the following ingredients:

| | |
|---|---|
| N-[p-(1-hexahydropyrimidin-2-one-yl)-phenethyl]-N'-(m-tolyl)-piperazine | 30 parts |
| Lactose | 70 " |
| Corn starch | 93 " |
| Sec. calcium phosphate | 47 " |
| Soluble starch | 3 " |
| Magnesium stearate | 3 " |
| Colloidal silicic acid | 4 " |
| Total | 250 parts |

Preparation

The active ingredient was admixed with part of the excipients, kneaded intensely with an aqueous solution of the soluble starch and granulated by passing it through a screen in the conventional manner. The dried granulate was admixed with the remaining excipients and compressed into tablets, each of which weighed 250 mgm. Each tablet contained 30 mgm of the piperazine compound and was an oral dosage unit composition with effective CNS-depressing activity.

EXAMPLE 76

Coated Tablets

The tablet core composition was compounded from the following ingredients:

| | |
|---|---|
| N[p-(1-imidazolidin-2,5-dione-yl)-phenethyl]-N'-(β-indanyl)-piperazine | 40 parts |
| Lactose | 50 " |
| Corn starch | 80 " |
| Sec. calcium phosphate | 50 " |
| Magnesium stearate | 3 " |
| Soluble starch | 3 " |
| Colloidal silicic acid | 4 " |
| Total | 230 parts |

Preparation

The active ingredient was admixed with part of the excipients, kneaded intensely with an aqueous solution of the soluble starch and then granulated in a conventional manner. The granulate was admixed with the remaining excipients and compressed into tablet cores, each weighing 250 mgm. The cores were coated with a thin shell consisting of talcum, sugar and gum arabic in known manner. Each coated tablet contained 40 mgm of the piperazine compound and was an oral dosage unit composition with effective CNS-depressing activity.

EXAMPLE 77

Suppositories

The suppository composition was compounded from the following ingredients:

| | |
|---|---|
| N-[p-(1-piperidin-2-one-yl)-phenethyl]-N'-(o-tolyl)-piperazine | 30 parts |
| Metamizol | 10 " |
| Lecithin | 2 " |
| Suppository base (e.g. cocoa butter) | 1790 " |
| Total | 1832 parts |

Preparation

The active ingredients, together with the lecithin, were dispersed homogeneously into the molten suppository base. 1832 mgm portions of the mixture were poured into suppository molds, and allowed to solidify. Each suppository contained 30 mgm of the piperazine compound and was a rectal dosage unit composition with effective CNS-depressing activity.

Analogous results are obtained when any one of the other arylpiperazine compounds embraced by formula I, or a non-toxic, pharmacologically acceptable acid addition salt thereof, is substituted for the particular arylpiperazine compound in Examples 75 to 77. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A racemic or optically active compound of the formula

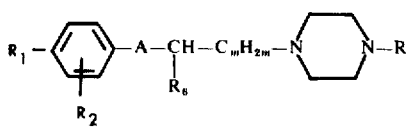

wherein

R is phenyl; phenyl having one or two substituents attached thereto, said substituents being selected from the group consisting of alkyl of 1 to 4 carbon atoms, alkoxy of 1 to 4 carbon atoms, alkylthio of 1 to 4 carbon atoms, chlorine and trifluoromethyl; naphthyl; tetrahydronaphthyl; indanyl; pyridyl; thiazolyl; or isoquinolyl;

$R_1$ is

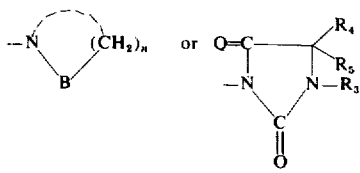

where

B is

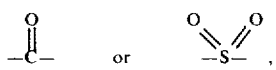

$n$ is 2 or 3

$R_3$ is hydrogen, alkyl of 1 to 4 carbon atoms, $R_4$ and $R_5$ are each hydrogen or alkyl of 1 to 4 carbon atoms, and Q is oxygen or two hydrogens, $R_2$ is hydrogen, alkyl of 1 to 4 carbon atoms, alkoxy of 1 to 4 carbon atoms or halogen, A is a single carbon-to-carbon bond or $-OCH_2-$, $R_6$ is hydrogen, hydroxyl, alkoxy of 1 to 4 carbon atoms or alkanoyloxy of 1 to 4 carbon atoms, and $m$ is 0, 1, 2, 3, 4 or 5, but other than 0 when $R_6$ is hydroxyl, or a non-toxic, pharmacologically acceptable acid addition salt thereof.

2. A compound of claim 1, which is N-[p-(1-pyrrolidin-2-one-yl)-phenethyl]-N'-(2',3'-xylyl)-piperazine or a non-toxic, pharmacologically acceptable acid addition salt thereof.

3. A compound of claim 1, which is N-[p-(1-piperidin-2-one-yl)-phenethyl]-N'-(o-tolyl)-piperazine or a non-toxic, pharmacologically acceptable acid addition salt thereof.

4. A compound of claim 1, which is N-[p-(1-isothiazolidin-1,1-dioxide-yl)-phenethyl]-N'-(2',3'-xylyl)-piperazine or a non-toxic, pharmacologically acceptable acid addition salt thereof.

5. A compound of claim 1, which is N-[p-(1-imidazolidin-2,5-dione-yl)-phenethyl]-N'-(β-indanyl)-piperazine or a non-toxic, pharmacologically acceptable acid addition salt thereof.

6. A compound of claim 1, which is N-[p-(1-imidazolidin-2,5-dione-yl)-phenethyl]-N'-phenyl-piperazine or a non-toxic, pharmacologically acceptable acid addition salt thereof.

7. A compound of claim 1, which is N-[p-(1-imidazolidin-2,5-dione-yl)-phenethyl]-piperazine or a non-toxic, pharmacologically acceptable acid addition salt thereof.

* * * * *